United States Patent [19]

Vlasbloem et al.

[11] Patent Number: 5,164,977
[45] Date of Patent: * Nov. 17, 1992

[54] PROCESS AND APPARATUS FOR EFFECTING SLIT RADIOGRAPHY

[75] Inventors: Hugo Vlasbloem, Maasland; Simon Duinker, Bloemendaal, both of Netherlands

[73] Assignee: B.V. Optische Industrie, "De Oude Delft", Delft, Netherlands

[*] Notice: The portion of the term of this patent subsequent to Dec. 22, 2004 has been disclaimed.

[21] Appl. No.: 665,291

[22] Filed: Mar. 5, 1991

Related U.S. Application Data

[63] Continuation-in-part of Ser. No. 306,348, Feb. 3, 1989, Pat. No. 5,005,915, which is a continuation-in-part of Ser. No. 648,707, Sep. 7, 1984, Pat. No. 4,803,714, and Ser. No. 464,407, Sep. 12, 1990, which is a continuation-in-part of Ser. No. 125,214, Nov. 25, 1987, Pat. No. 4,984,258, which is a continuation of Ser. No. 713,309, Mar. 18, 1985, abandoned.

[30] Foreign Application Priority Data

Sep. 13, 1983 [NL] Netherlands .......................... 8303156
Mar. 16, 1984 [NL] Netherlands .......................... 8400845

[51] Int. Cl.⁵ .............................................. G21K 1/00
[52] U.S. Cl. .................................. 378/146; 378/145; 378/151; 378/157
[58] Field of Search ................... 378/62, 108, 145-147, 378/150, 152, 153, 151, 156-158

[56] References Cited

U.S. PATENT DOCUMENTS

| 2,837,657 | 6/1958 | Craig et al. | 378/146 |
| 3,766,387 | 10/1973 | Heffan et al. | 378/146 |
| 3,832,546 | 8/1974 | Morsell et al. | 378/146 |
| 3,924,133 | 12/1975 | Reiss | 378/62 |
| 4,433,430 | 2/1984 | Fredzell | 378/146 |
| 4,675,893 | 6/1987 | Duinker et al. | 378/145 |
| 4,715,056 | 12/1987 | Vlasbloem et al. | 378/145 |
| 4,785,471 | 11/1988 | Boersma | 378/145 |
| 4,803,714 | 2/1989 | Vlasbloem | 378/146 |
| 4,984,258 | 1/1991 | Vlasbloem et al. | 378/145 |
| 5,008,915 | 4/1991 | Vlasbloem | 378/145 |

FOREIGN PATENT DOCUMENTS 0063644 11/1982 European Pat. Off. ............ 378/108

*Primary Examiner*—David P. Porta
*Attorney, Agent, or Firm*—Louis E. Marn

[57] ABSTRACT

A slit radiography assembly including an X-ray source, and X-ray detector and a slit diaphragm comprised of a plurality of sections juxtaposed in the longitudinal direction of the slit and coacting with controllable attenuation elements wherein: during scanning, a detection assembly includes a plurality of response sections cooperate with the X-ray detector to provide an electric signal representative of the intensity to control the attenuation elements during scanning at initial measuring exposure and subsequent radiographical exposure of the body.

1 Claim, 2 Drawing Sheets

PROCESS AND APPARATUS FOR EFFECTING SLIT RADIOGRAPHY

BACKGROUND OF THE INVENTION (1) Related Application

This is a continuation-in-part application of U.S. application Ser. No. 078/306,348, filed Feb. 3, 1989 (now U.S. Pat. No. 5,008,915), which is a continuation-in-part of U.S. application Ser. No. 06/648,707, filed Sep. 7, 1984 (now U.S. Pat. No. 4,803,714), and of U.S. application Ser. No. 07/464,407, filed Jan. 12, 1990 which is a continuation-in-part of U.S. application Ser. NO. 07/126,214, filed Nov. 25, 1987 (now U.S. Pat. No. 4,984,258), which is a continuation of U.S. application Ser. No. 06/713,309, filed Mar. 18, 1985 (now abandoned).

(2) Field of the Invention

This invention relates to slit radiography, and more particularly to an improved process and apparatus for effecting slit radiography.

(3) Brief Description of the Prior Art

In an article entitled "Schlitzaufnahmetechnik mit mitgeführtem Strahler" by R. Moore and K. Amplatz, published in Elektromedica 1/81, there is disclosed an apparatus comprised of an X-ray source capable of irradiating a patient through a slit diaphragm and having a second slit diaphragm disposed on the other side of the patient whereby the second slit diaphragm permits radiation passing through the patient to pass to an X-ray screen-film combination. In operation, the X-ray source is pivoted along with the first slit diaphragm and the second slit diaphragm, so that the patient is, as it were, scanned strip-wise, and the picture to be formed is built-up in strips.

One advantage of slit-scanning technique, over and above conventional techniques, is that a lower radiation dosage can be used so that the irradiation load on a patient is less, and the effect of scattered radiation can be more effectively suppressed, to produce clearer pictures. A disadvantage of known slit-scanning techniques is that a second slit diaphragm is needed as well as a large X-ray screen.

In an article "Computer assisted exposure in scanned film radiography", by D. B. Plewes in Proceedings International Workshop on Physics and Engineering in Medical Imaging, March 1982, pp. 79 ff., there is disclosed a method of image harmonization in slit radiography. According to the article, the moving slit diaphragm coacts with a second moving slit diaphragm placed transverse to the first, so that a relatively small moving diaphragm is produced of more or less rectangular or diamond-shaped configuration. Consequently, the body being irradiated is scanned, in fact according to the flying-spot system an X-ray film cassette is placed behind the body being irradiated. Behind the cassette there is positioned a detector which measures the radiation passing through the film cassette instantaneously. Depending on the value measured, the adjustment of the X-ray source and thereby both the intensity and the X-ray spectrum are controlled.

Although the Plewes article therefore, like the present invention, relates to dynamic image harmonization, the method described in the Plewes article is based on a different basic idea, since it does not concern local adjustment of the slit width of the diaphragm at a given setting of the X-ray source. A further drawback going with the technique disclosed in the above article, is that an expensive controllable X-ray source is required. Another drawback is that by application of the flying-spot system, effective use of the X-rays generated is slight, because the major part of the radiation is suppressed by the coacting moving slit diaphragm. For obtaining a usable diaphragm aperture, consequently, an overdiamensioned X-ray source is required. Moreover, relatively long scanning times will be necessary. Furthermore, in the technique disclosed in the article, measurement takes place behind the film cassette, so that the X-ray spectrum is affected, with the result that the control of the X-ray source adjustment is not optimum for parts of the patient that cause little attenuation of the X-rays.

Reference is also made to the article "Digitally controlled beam attenuator" by Peppler et al., published in SPIE, Vol. 347, Application of Optical Instrumentation in Medicine C, 1982, pp. 106 ff., describing a method of obtaining a harmonized X-ray shadow image. According to the technique described by Peppler et al., use is made of a matrix of attenuation elements, the attenuation of which can be adjusted individually. After adjustment of the attenuation elements, a patient is X-rayed. The Peppler et al. method therefore does neither concern slit radiography nor dynamic image harmonization and moreover is time-consuming.

OBJECTS OF THE INVENTION

An object of the present invention is to provide improved methods for forming radiographs overcoming the disadvantages hereinabove disclosed.

Another object of the present invention is to provide improved methods for forming radiographs at lower radiation dosages.

One important advantage of the invention is that, in the X-ray detector, an intensification can be accomplished by a suitable selection of the electrical field intensity. As a consequence, a lower dosage of radiation can be used.

A further object of the present invention is to provide methods for forming radiographs using slit radiography wherein effects of patient's dimensions are compensated during exposure of the film.

A still further object of the present invention is to provide an improved process and apparatus for effecting slit radiography with enhanced contrast intensity and contrast range.

Still another object of the present invention is to provide an improved process and apparatus for effecting slit radiography whereby smaller differences are contrasted or achieved with reference to soft and hard parts.

SUMMARY OF THE INVENTION

These and other objects of the present invention are achieved by methods of forming a radiograph assembly by providing a detector coacting with the X-ray detector and comprising a plurality of sections juxtaposed in the longitudinal direction of the strip-like portion of the X-ray detector irradiated through the slit diaphragm wherein each section is adapted to produce an electric signal depending upon the radiation impinging instantaneously on the associated section of the X-ray detector, and wherein the slit diaphragm is comprised of a plurality of sections juxtaposed in the longitudinal direction of the slit coacting with at least one controllable attenuation element, and corresponding with the number of sections of the detection member, and wherein there is provided a control which during the scanning movement instantaneously and simultaneously adjust the quantity of X-rays passed per section of the diaphragm, under the control of electric signals generated by the detector, wherein the X-ray source during a first scanning of the object at a low level of radiation is used to determine proper setting of the X-ray source for a second scanning of the object for forming a radiograph at a higher energy level whereby the operational setting of the X-ray source is adapted to the specific properties of the body to be examined in a simple manner.

BRIEF DESCRIPTION OF THE DRAWINGS

The invention will be more clearly understood with reference to the following detailed description of the invention when taken with the accompanying drawings, in which.

DETAILED DESCRIPTION OF THE DRAWINGS

Figure 1:
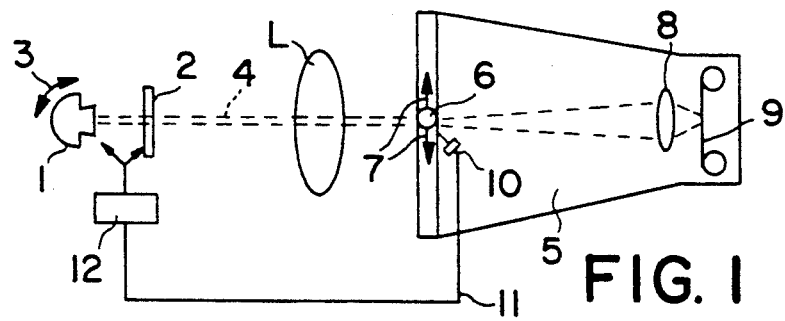
FIG. 1 is a diagrammatic side view of an embodiment of an apparatus for slit radiography according to the present invention.

Referring now to the drawings and in particular to FIG. 1, there is illustrated an apparatus for slit radiography comprised of an X-ray source 1 having a slit diaphragm 2 adapted to perform a swivelling movement, as indicated by arrow 3, effects a scanning movement. A scanning movement of the X-ray source can also be obtained when the X-ray source is stationary and the slit diaphragm performs a translational movement transversely to the longitudinal direction of the slit, possibly accompanied by a swivelling movement, or when the diaphragm is stationary and the X-ray source performs a translational and possibly a swivelling movement.

Opposite the slit diaphragm 2, there is provided a casing 5 positioned at such an interspace that there remains room for a body L to be irradiated, the casing includes an X-ray detector 6 having an entrance face sufficiently large to collect radiation passing at any moment through the body being irradiated during swivelling movement of the X-ray source and the slit diaphragm. An elongate tubular detector of the proximity focus type may be employed for converting collected X-rays into a light image, thereby effecting a vertical movement, in synchronism with the swivelling of the X-ray source, as indicated by arrows 7. An instantaneous strip-like light image provided by the detector is projected on a film 9 by means of a lens system 8, shown diagrammatically, for forming a complete image from successively projected strip-like images. As more fully hereinafter described, the X-ray film 9 is covered during the scanning step.

According to the present invention, there is positioned adjacent the X-ray detector 6, a light detection device 10 which, as viewed in a direction transverse to the plane of drawing, comprises a plurality of juxtaposed sections, each measuring the quantity of light generated by a corresponding opposite portion of the exit face of the X-ray detector 6. For the embodiment shown, light detection device 10 moves along with the X-ray detector 6. The quantities of light measured by the sections of the light detection device 10 are converted in known manner into electric signals supplied simultaneously through lead 11 to controller 12, shown diagrammatically. The controller is adapted to locally adjust the width and/or transmissivity to X-rays of the slit diaphragm consisting of a plurality of sections corresponding with the number of sections of the light detection device 10. Slit width and/or transmissivity characteristic of each f the diaphragm sections can be adjusted separately by one of the methods hereinafter described.

Adjustment of the diaphragm sections is effected, according to the present invention, during X-raying, so that a dynamic instantaneous exposure control is achieved and the film 9 exposed in an optimum manner at any moment. An additional advantage is that there is thus obtained a noise equalization so that the signal-to-noise ratio is substantially constant throughout the entire image which is especially of importance when digital techniques of X-ray diagnostics are used. The light detection device 9 is placed in such a manner that this does not interfere with the passage of rays between the X-ray detector 6 and the lens system 8.

Figure 2A:
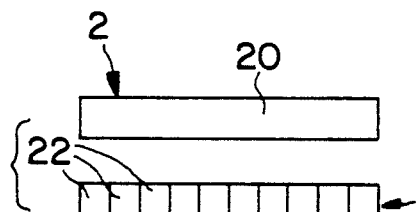
FIGS. 2a and 2b diagrammatically show an embodiment of slit radiography which can be used in the apparatus shown in FIG. 1.
Figure 2B:
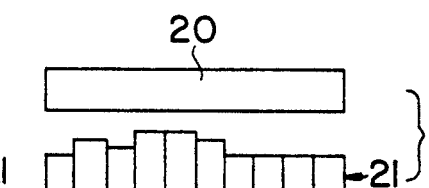

FIG. 2a diagrammatically shows an embodiment of a slit diaphragm for an apparatus according to the present invention comprised of an upper portion 20, which may be made of lead, and a lower portion 21, which comprises sections 22 slidable relatively to each other in the direction of the upper portion. The sections 22 may also be made of lead. FIG. 2b shows a possible position of the slidable section 22 at a given moment during X-raying. The sections indicated by arrows have been shifted in the direction of the upper portion of the diaphragm so as to reduce the slit width of the diaphragm at that location. The extent of shift at some particular moments depends on the quantity of light measured by the corresponding section of the light detection device 10. In the embodiment shown, ten slidable sections are used that correspond with ten light detection sections. In thorax radiography, a satisfactory result can be obtained with such a number of sections. If desired, a different number of sections can of course be used.

Figure 3:
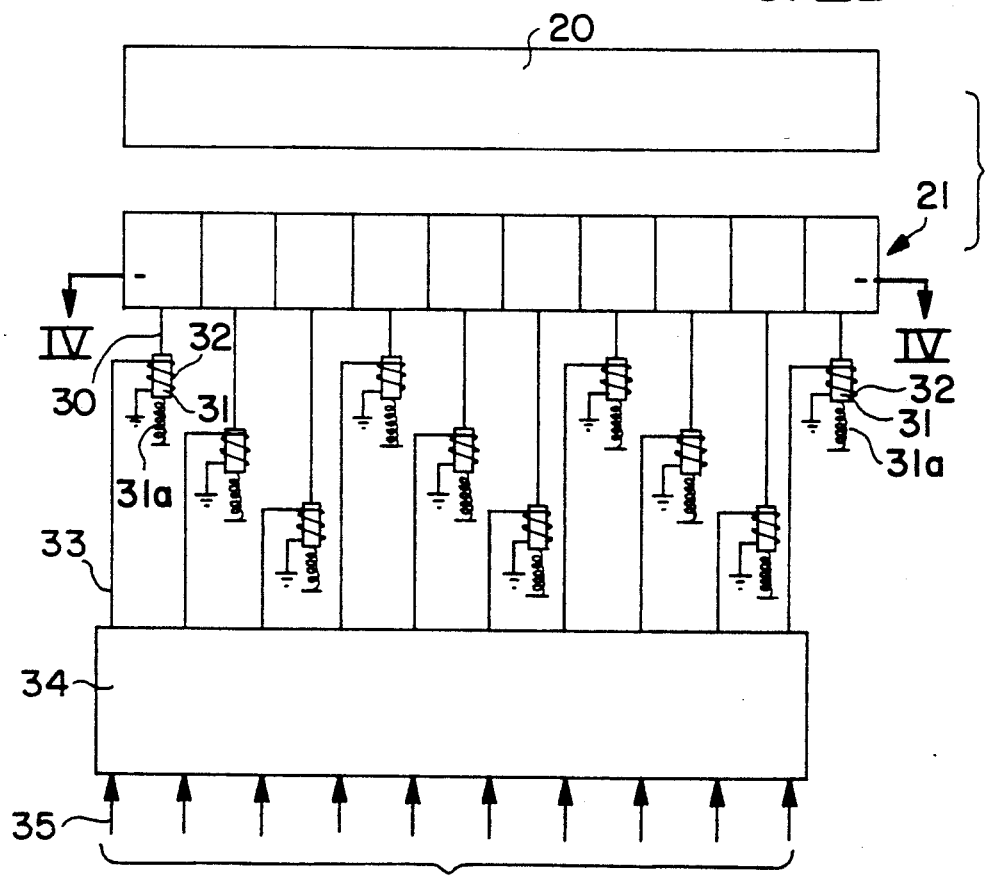
FIG. 3 shows a manner of controlling the slit diaphragm shown in FIGS. 2a and 2b.

FIG. 3 diagrammatically shows a manner of control of the sections of the slit diaphragm shown in FIG. 2. The sections of the diaphragm portion 21 are each connected by means of a stationary member 30, e.g. a small rod, to a coil core 31, e.g. of soft iron, which is adapted to slide in a coil 32, and which can be maintained in the rest portion by resetting means, such as spring means 31a or a magnet. Each coil is energized by an output 33 of a control device 34. The control signal appearing at each output 33 depends on an input signal appearing at a corresponding input 35 of the control device and originating from the associated section of the light detection device 10. The current intensity through a coil determines the position of the associated soft iron core and hence the position of the diaphragm section coupled therewith. It is observed that in the embodiment shown, only one of the members of the slit diaphragm has slidable sections. Naturally, it is also possible to provide both members of the slit diaphragm with slidable sections. It is further noted that the slidable sections of a diaphragm member are placed jointly in a supporting member. The construction of such a supporting member is obvious to one skilled in the art and hence will not be described herein.

Figure 4A:
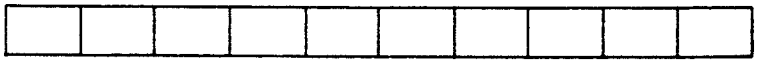
FIG. 4a-4c show some embodiments of a slit diaphragm shown in FIGS. 2a and 2b.
Figure 4B:
Figure 4C:

The slidable sections of the one member of the slit diaphragm shown in FIGS. 2 and 3 may have a rectangular cross-sectional configuration, as shown in FIG. 4A, showing a cross-section on the line IV—IV of FIG. 3. In that case interspaces or transitions between the sections could lead to a line effect in the eventual radiograph. In order to reduce the chance thereof, the sections of the slit diaphragm may each be trapezoidal in cross-section, as shown in FIG. 4B, showing a cross-section corresponding with that of FIG. 4A. Other variants are conceivable too, e.g. as shown in FIG. 4C, wherein the sections engage with each other by means of a tongue and groove joint.

Figure 5:
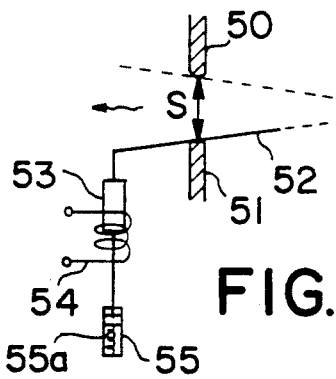
FIG. 5 shows a slit diaphragm and the manner in which the effective slit width can be controlled locally.

FIG. 5 shows a diagrammatic side view of a different embodiment of a slit diaphragm which can be employed in an apparatus according to the present invention and which is based on two stationary diaphragm members 50 and 51 defining a stationary slit S. For the purpose of orientation, FIG. 5 shows the X-ray source 1 diagrammatically. The slit S contains a plurality of juxtaposed elongate attenuation elements, one of which is shown at 52 in FIG. 5. Attenuation element 52 extends through the slit S and is adapted to pivot relatively to one of the stationary diaphragm portions, in this embodiment the lower portion 51, or relatively to a suitably placed carrier. Adjacent the one end of the attenuation element 52, in the same manner as described for the sections shown in FIG. 3, this is coupled with a slidable soft iron core 53 of a coil 54. The soft iron core is further connected to an attenuation element 55 adapted to prevent the core 53 from slipping upon energization of the coil. Besides, a return spring is provided, in this embodiment a compression spring 55a, placed in the attenuation element.

In this embodiment, the other end of the attenuation element 52 points to the X-ray source and, by control of the coil 54, can extend into the X-ray beam through the slit S to a greater or lesser extent, in order to intercept the same at least partly. The attenuation elements may be made of lead, but also of other suitable material attenuating X-radiations, as e.g. soft iron, bronze, gold etc.

Figure 6:
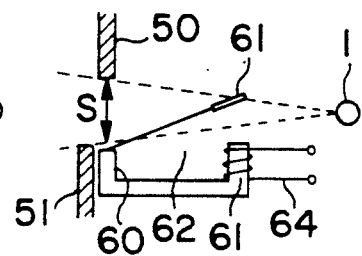
FIG. 6, 7 and 8 show variants of FIG. 5.
Figure 7:
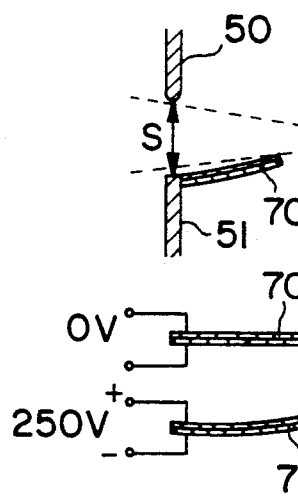
Figure 8:
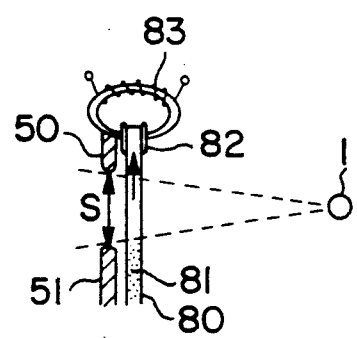

FIG. 6 shows a variant of FIG. 5. In the embodiment shown in FIG. 6, the stationary members of the slit diaphragm are again indicated at 50 and 51. Between the X-ray source 1 and the slit diaphragm there is placed a U-shaped yoke of soft iron, one leg 60 of which lies adjacent the slit diaphragm and the other leg 61 is spaced apart therefrom. Attached to the top of the one leg 60 is a resilient tongue 62, which extends obliquely upwards and carries at the other end a plate of magnetic material, e.g. magnet stell, disposed above the other leg 61. Besides, a coil 64 energizable by a control device, comparable to the control device 34 of FIG. 3, is wound about leg 61. Depending on the control of coil 64, the plate 63 is attracted to a greater or lesser extent by the leg 61 and the plate attenuates the X-radiation passed through slit S to a greater or lesser extent.

It is observed that for controlling the slit width along the entire length of slit S, a plurality of such yokes having resilient tongues as described, are juxtaposed. It is further observed that in principle the yoke could be placed in such a manner that the leg having the coil 64 is disposed adjacent the diaphragm and the resilient tongue is attached to the leg spaced apart from the diaphragm. Furthermore, in both cases the yoke may be positioned at the other side of the diaphragm, i.e. the side away from the X-ray source.

When use is made of sliding elements, as shown in FIGS. 2–4C, or of elongate elements, as shown in FIGS. 5 and 6, the instantaneous position thereof can also be controlled by a miniature stepping motor having an eccentric connected to the element to be controlled by means of e.g. a rod. Each element then requires a stepping motor. The control signals for the stepping motor are provided by the control means 12. It is true that when stepping motors are used, only a number of discrete positions of the attenuation elements can be adjusted, but this number may be sufficiently large, e.g. one hundred, to ensure satisfactory operation.

In order that an optimum X-ray dosage may be selected for a radiograph of an individual patient, according to the present invention, there is first made a measuring exposure. In making a measuring exposure, after the patient or the object to be X-rayed has been placed in position, the X-ray source 1 is energized so that it emits radiation at a level lower by a factor of about 10 than the average level used for normal exposure. The X-ray source 1 moves, for example, from the bottom angular position to the top angular position, with the X-ray image intensifier moving along with it correspondingly. During a certain part of the X-ray image intensifier's path (the measuring field), the average level of the light generated by the X-ray detector 6 is measured by means of the light detection device 10. The size of the measuring field can be selected as desired. In experiments, a measuring field of 10×20 cm. has proved satisfactory. As, for example for thorax exposures, the X-ray detector 6 should be at least 40 cm. long, the measuring field may accordingly be narrower than the field covered by the X-ray detector 6 without any objections.

Depending on the light value measured, the X-ray dosage needed for the actual exposure can now be set at an optimum value either manually or automatically. In the latter case, the output signal from the light detection device 10 controls the voltage of the X-ray detector 6 or the current through the X-ray tube 1. It is noted that the measuring exposure takes place without an exposure of the film 9. The film 9 may be covered or positioned for the actual exposure. When the X-ray source 1 is properly set, the X-ray source 1 is pivoted in the opposite direction, with the X-ray detector 6 moving along with it for making the actual radiograph.

During the measuring exposure and actual exposure, electric signals generated in the light detection device 10 are passed to the controller 12 to control the attenuating elements 22 during the respective measuring and actual exposures processing steps. The measuring signals obtained during the measuring exposure step may be stored and used in the actual exposure step. Generally, the making of a radiograph including measuring exposure is effected in about ten seconds.

In the method of forming a radiograph, a dosimeter, such as described in either copending U.S. application Ser. No. 06/931,538 now U.S. Pat. No. 4,896,041 or Ser. No. 06/931,539 now U.S. Pat. No. 4,859,855, filed Nov. 14, 1986, the substance of which is hereby incorporated by reference, may be used in lieu of the X-ray detector 6. Accordingly, the measuring step, as hereinabove described with reference to FIG. 1, is effected during which time a large X-ray film 9 disposed in a cassette (not shown) is covered (or is subsequently positioned in the cassette) whereby the dosimeter measures radiation intensity levels. The exposure step is effected with concomitant scanning with the dosimeter with the X-ray film 9 being uncovered to permit exposure thereof to imaging radiation with concomitant sector wise attenuation of the planar X-ray beam and the higher energizing level of the X-ray source 1.

The method of the present invention may be effected with a two-dimensional dosimeter of like dimension to the X-ray film 9, wherein such a dosimeter provides attenuated measuring signals during the measuring or first scanning step. The measuring signals obtained during the measuring step or first scanning run are used not only to effect beam sector modulation but also to determine intensity level of the X-ray source 1 during the imaging step or second scanning.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed is:

1. An apparatus for slit radiography, which comprises:

an X-ray source an X-ray detector for collecting radiation passing through a body to be radiographed;

a slit diaphragm positioned between said X-ray source and said body for forming a substantially planar X-ray beam;

a plurality of attenuating elements positioned along said slit diaphragm forming a plurality of attenuating sections;

means for scanning said body with said planar X-ray beam during an initial measuring exposure of said body at a predetermined level of radiation of said X-ray source and at a second radiographed exposure of said body at a higher level of radiation of said X-ray source;

detection means cooperating with said X-ray detector and comprising a plurality of response sections juxtaposed along a direction of said slit diaphragm, each of said response sections being responsive to radiation collected on said X-ray detector to produce an electric signal represenative of intensity of thus collected radiation, each of said response sections of said detection means corresponding to a respective attenuating section of said plurality of attenuating sections; and means for simultaneously controlling each of said attenuating sections during scannings of said body in response to said electric signal produced at respective response sections of said detection means.

* * * * *